United States Patent
Arodzero et al.

(10) Patent No.: US 10,481,113 B2
(45) Date of Patent: Nov. 19, 2019

(54) X-RAY BACKSCATTER INSPECTION SYSTEM

(71) Applicant: Radiabeam Technologies LLC, Santa Monica, CA (US)

(72) Inventors: Anatoli Arodzero, Billerica, MA (US); Sergey V. Kutsaev, Santa Monica, CA (US); Vitaliy Ziskin, Newton, MA (US)

(73) Assignee: Radiabeam Technologies, LLC, Santa Monica, CA (US)

( * ) Notice: Subject to any disclaimer, the term of this patent is extended or adjusted under 35 U.S.C. 154(b) by 277 days.

(21) Appl. No.: 15/601,155

(22) Filed: May 22, 2017

(65) Prior Publication Data

US 2017/0336526 A1     Nov. 23, 2017

Related U.S. Application Data

(60) Provisional application No. 62/339,883, filed on May 22, 2016.

(51) Int. Cl.
*G01N 23/203* (2006.01)

(52) U.S. Cl.
CPC ..... *G01N 23/203* (2013.01); *G01N 2223/053* (2013.01)

(58) Field of Classification Search
None
See application file for complete search history.

(56) References Cited

U.S. PATENT DOCUMENTS

2010/0158192 A1* 6/2010 Friederich ............ G01V 5/0016
378/57
2017/0358380 A1* 12/2017 Rothschild ........... G01V 5/0025

* cited by examiner

*Primary Examiner* — Hoon K Song

(57) ABSTRACT

Apparatus and methods for Compton scattering radiography employing a variable energy X-ray source and a detector capable of detecting the temporal intensity profile of scattered X-ray pulses disposed on one side of an object to be imaged. Based on analysis of the measurement of the instantaneous intensity of the detected photons and the beam position relative to the object, an image is generated. Each voxel can be reconstructed to yield a measure of variation in the density of the material of the object.

20 Claims, 14 Drawing Sheets

Composite test object used to demonstrate tomographic imaging properties of the backscatter technique.

Demonstration of X-ray backscatter tomography by subtraction of two images made in different energies: a) a backscatter image of the test object, Figure 6, made at 140 keV; b) an image at 90 keV; c) the tomographic image plane containing the PSU letters generated by subtracting a) and b).

Desirable energy and current profiles of X-ray pulses. Top: System with AC triode X-ray tube. Bottom: System with electron linac as an X-ray source. In the case of X-ray tube, the typical duration of the pulse can be about 4 ms; energy ramp can be from ~70 to 340 keV. For a system with linac, pulse duration will be shorter; maximum end-point energy can be up to 1 MeV or higher.

X-RAY BACKSCATTER INSPECTION SYSTEM

This application claims the benefit of U.S. Provisional Application No. 62/339,883 titled "X-ray Backscatter inspection System" filed May 22, 2016. The entire disclosure of the above application including appendixes is incorporated herein by reference.

FIELD

This invention relates to radiographic imaging of objects by Compton scattering More particularly, the invention relates to methods and apparatus for providing images indicative of variations in density of the interior of objects, wherein the examination process may be carried out entirely from one side of the object.

BACKGROUND

X-ray imaging techniques based on Compton backscatter allow inspection and screening of cargo sea- and air-containers, a variety of vehicles, small ships, luggage, and suspicious packages. Government agencies, border authorities, law enforcement personnel, military organizations, and security services in more than 65 countries widely use such systems. For example, more than 750 mobile backscatter systems sold to date. In contrast to commonly used transmission inspection systems, backscatter imaging involves positioning both source and detectors on only one side of a target object. Such systems are exclusively useful in situations where access to the far part of the inspected object is limited, making X-ray transmission system impractical.

Compton backscatter imaging (CBI) is a single-sided imaging technique in which the radiation source and the detection/imaging device are located on the same side of the object. As a result, CBI is a valuable non-destructive inspection (NDI) tool because of its single-sided nature, the penetrating abilities of radiation, and unique interaction properties of radiation with matter. Changes in the backscatter photon field intensity (resulting in contrast changes in images) are caused by differences in absorption and scattering cross sections along the path of the scattered photons. Since the inception of CBI, a diverse set of imaging techniques have evolved using both collimated and un-collimated detectors, coded apertures, and hard X-ray optics. "Pencil beam" CBI uses a highly collimated beam of radiation to interrogate objects. The pencil beams may vary in diameter from microns to centimeters, but usually consist of a near-parallel array of photons forming a tight beam. A detector measures the backscatter from the CBI pencil beam as it scans the object.

The rate at which the X-rays are scattered from a region is indicative of its density; since Compton-scattering of X-rays takes place from electrons of individual atoms, less scattered X-rays emerge from the material when the material is denser. This fact is known to the prior art to be useful in generating images of structures using Compton scattering.

The attenuation of photons of the energies less than 1 MeV is composed of Compton scattering, photoelectric absorption and to a small degree coherent scattering. FIG. 3 shows the contribution of Compton scattering to the total attenuation for several elements as a function of energy. In the region up to 1 MeV, the dominant process of interaction is photoelectric absorption, which is raises with atomic number. Therefore, for light elements backscatter radiation will be more intensive compare with materials with higher Z. This is the reason why in backscatter images light object (low Z) looks brighter compare with high Z objects.

The backscatter signal is dependent upon the atomic number, density and thickness of the material under test and the incident energy spectrum of the photons. FIG. 4 shows the total backscatter as a function of thickness of acrylic and aluminum for two Bremsstrahlung incident spectra at 55 and 110 keV.

At 110 keV an infinite thick acrylic layer would backscatter approximately 25% of the incident energy and an aluminum layer about 7%. The depths where 75% of the maximum backscatter is reached are 5 cm in acrylic and 1 cm in aluminum.

Conventional backscatter inspection systems have a significant limitation in their ability to penetrate even moderately dense cargos. Moreover, the signal is dominated by the first interrogated layer, typically metal wall of the container or a vehicle or the fiberglass hull of a boat.

FIG. 1 illustrates a conventional X-ray backscatter cargo inspection system as has been described in D-C. Dinca, J. R. Schubert, J. Callerame. X-ray Backscatter Imaging, Proc. Of SPIE, Vol. 6945, 694516, (2008) doi:10.1117/12.773334, which is incorporated herein by reference.

The X-ray pencil beam is created by the rotating collimator 107 on the right and is scanned vertically while the object being inspected moves horizontally. The X-ray beam 102 itself passes between two large backscatter detectors 104, and scattered X-rays 103 are collected and registered by detectors 104 at each beam position.

To overcome this fundamental limitation, we have developed an advanced concept for backscatter system that uses the intrapulse ramp of the electron beam energy of the X-ray source. We propose improving on the conventional backscatter systems based on the continuous beam X-ray tubes, or "quasi-continuous" linac with energy- and current-modulated pulses, fast X-ray backscatter detectors, and algorithm of image "peeling" processing.

In this approach, we temporally encode the sensitivity to multiple layers of the imaged cargo. By sequencing the end-point energy of the X-ray beam in a predictable manner, we separate the backscatter signals originating from various depths of the cargo. The proposed concept represents an extension of the approach proposed for transmission inspection systems as have been described in A. Arodzero. Scintillation-Cherenkov detector and method for high-energy X-ray cargo container imaging and industrial radiography, US Patent Application 2011/0163236 and A. Arodzero, S. Boucher, A. Murokh, S. Vinogradov, S. Kutsaev, System and Method for Adaptive X-ray Cargo Inspection, US Patent Application 2015/0338545 and A. Arodzero, S. Boucher, J. Hartzell, S. Kutsaev, R. C. Lanza, V. Palermo, S. Vinogradov, V. Ziskin, High Speed, Low Dose, intelligent X-ray Cargo Inspection. IEEE-2015 Nuclear Science Symposium proceedings, paper N2B1-6 which are incorporated herein by reference.

OBJECTS AND SUMMARY OF THE INVENTION

Conventional backscatter inspection systems have a major limitation in their ability to penetrate even moderately dense cargos. Moreover, the image is dominated by the first interrogated layer, typically metal walls of the container or a vehicle. In order to overcome these limitations, we have developed an advanced concept for a novel X-ray backscatter inspection system based on the intrapulse ramp of the electron beam energy of the X-ray source, tiled array of fast detectors, and algorithm of image "peeling" processing. In contrast to conventional backscatter system, which uses continuous beam X-ray tubes, or "quasi-continuous" linac, we proposed concept with energy- and current-modulated X-ray pulses.

It is an object of the invention to provide a method and apparatus for imaging the interior of an object using Compton scattering techniques, wherein both a source of irradiating variable-energy X-rays and a detector of scattered X-rays may be disposed on the same side of an object to be imaged.

It is a further object of the invention to provide a method and apparatus for performing a reconstruction of an image of an interior of an object 101, where a source of variable energy X-rays is used to irradiate the object 101 and an X-ray detector 104 is used to detect Compton-scattered X-rays 103, and where the source 102 and detector 104 are disposed on the same side of the object 101 with the detector and X-ray source contained in an appropriate housing 105.

These and other objects of the invention appearing in the discussion below are satisfied according to the present invention, whereby a pencil beam of variable energy X-rays 202, FIG. 2, generated by pulse X-ray generator 207, is employed to irradiate an object 202 to be inspected. A detector capable of detecting scattered pulse X-rays 204 and measuring their intensity is employed to detect X-rays 203 having been Compton-scattered. The intensity of the detected X-rays are recorded, together with the respective detector locations and information about the irradiating X-ray source. A number of data acquisitions are performed, each involving the steps of selecting the energy characteristics of the irradiating X-ray source, irradiating the object and detecting the scattered X-ray intensity. The intensity of the scattered X-rays is determined and used to identify material density within the object Since we integrate lower- and higher-energy portion of ramping (modulated) energy X-ray pulse, it is not necessary to have detector capable to detect individual X-rays. However, in multiple embodiments, the detector is fast enough to provide temporal intensity profile of X-ray pulse. In case of scintillation detector, the decay time of scintillator need to be about two order magnitude lower than X-ray pulse duration.

The instant disclosure can overcome these limitations with an advanced concept for a novel X-ray backscatter inspection system based on the intrapulse ramp of the electron beam energy of the X-ray source, tiled array of fast detectors, and method of image "peeling" processing.

An X-ray tube 207 or linear accelerator 1301, can be used for generate ramping X-ray pulses. In the case of an X-ray tube 207, the typical duration of pulse, in one embodiment, can be about 4 ms, with the energy ramp from about 70 keV to about 340 keV. In an alternative embodiment for system utilizing a linac accelerator as the X-ray source the pulse duration can be shorter, and the maximum end-point energy can be up to 1 MeV or higher.

In one embodiment, the instant system is a novel X-ray backscatter inspection system using an intrapulse ramp of the electron beam energy of the X-ray source, tiled array of fast detectors, and method of image "peeling" processing.

One embodiment incorporates the steps of:
Collect detector pixel data from all pulse energies;
Estimate areal electron density from the slope of the backscatter signal;
Divide backscatter signal into low and high energy components;
Subtract weighted low energy signal from high energy signal; and Render "behind the wall" image.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred embodiments, reference is made to the accompanying drawings, which form a part hereof, and within which are shown by way of illustration the practice of specific embodiments of systems and methods for scanning an object from a perspective that is substantially orthogonal to an inspection space. It is to be understood that other embodiments may be utilized, and that structural changes may be made and processes may vary in other embodiments.

Figure 2:
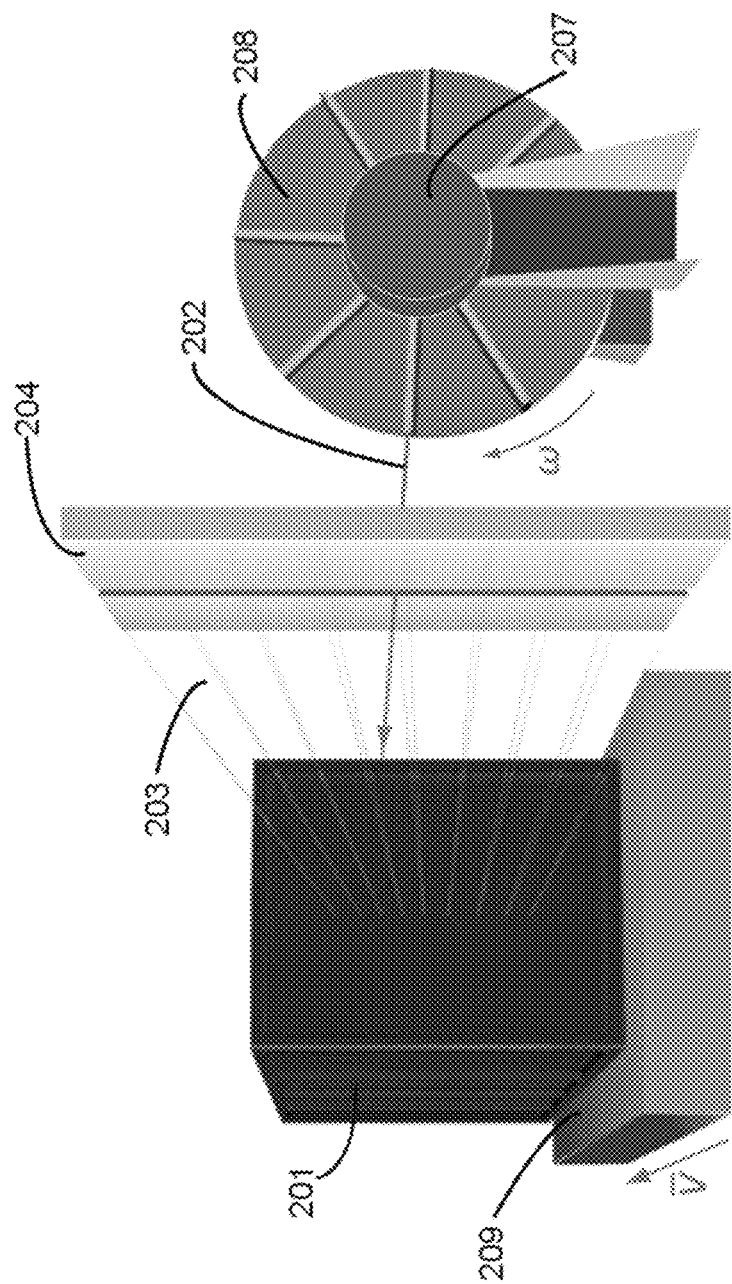
FIG. 2. Schematic layout of the instant system employed energy modulated X-ray pulses.

It is an object of the invention to provide an image responsive to variation in the density of an object 201 using a variable energy X-ray source 207 and X-ray detectors 204 disposed on one side thereof. FIG. 2 shows schematically a perspective view of a suitable source 207 and detector 204 arrangement. The X-ray pencil beam 202 is created by the rotating collimator 208 and is scanned vertically while the object 201 being inspected moves horizontally, in this case on a conveyor belt 209. According to one embodiment of the invention, a source emitting a pencil beam of X-rays rays 202, typically in the range of approximately one hundred keV to several hundred keV is put adjacent to the object 201. In this energy regime Compton scattering is the dominant scattering mechanism.

In one embodiment, the instant system is a novel X-ray backscatter inspection system using an intrapulse ramp of the electron beam energy of the X-ray source, tiled array of fast detectors, and method of image "peeling" processing. In contrast to conventional backscatter system, which uses continuous beam X-ray tubes, or a conventional linac, we employ sources that generate energy- and current-modulated pulses.

It is a further object of the invention to provide a means to identify the different materials constituting the object as a function of their respective depths within the object. The object may comprise a first material in a first layer and a second material in a second layer.

The system has an X-ray source 207 configured to deliver an X-ray beam 202 onto the object 201 and cause secondary X-rays 203 that have been Compton scattered from the object 201. The X-rays from source pass into the object and are Compton-scattered from electrons of atoms of the materials therein. Where the material of the object being imaged is less dense, a relatively larger proportion of the X-rays are scattered toward the surface and are less attenuated thus they may be detected by a detector. The detector 204 can measure the flux of the detected X-rays 203, and of noting the specific location at which the X-ray flux is detected. Where the source is juxtaposed to a less dense object, a relatively substantial fraction of the incident X-rays can be expected to be Compton scattered and detected by the detector. A somewhat lesser fraction of the incident X-rays will be scattered from more dense material and will also be detected by the detector. More specifically, the relative proportion of X-rays re-radiated from the denser materials and the less dense materials is a function of the respective densities of these materials, since Compton scattering is a probabilistic effect varying with the density of electrons in the material but with rescattering of the lower energy backscattered X-rays in the material on the return trip out of the material.

To provide for imaging of the object using Compton scattered photons the scattered photons will be scattered primarily in the backward direction. Scattering in the backward direction allows for the detectors to be configured on the same side of the object as the X-ray source. In one embodiment, the X-ray detector 204 is configured relative to the X-ray source 207 and the object 201 to measure Compton scattered X-rays 203 that have been scattered from the object 201 between about 140 degrees to 180 degrees. A larger range could also be used but in most circumstances for large objects attempting to measure Compton scatter form smaller angles in geometrically difficult. In cases of large objects where access to smaller scattering angles is not feasible, a better embodiment could be that the X-ray detector is configured to measure scattered X-rays that have been scattered from the object between about 160 degrees to 179 degrees.

In various embodiments, the system has an X-ray source with an adjustable energy output. There are at least two possible X-ray sources: a source generated Bremsstrahlung spectrum—characterized by the end-point energy of the resulting spectrum; and a monochromatic modulated/adjustable (ramping up or ramping down) energy source, for example based on free electron laser.

The X-ray source illuminates the object with X-rays and the X-ray detector measures the integrated flux of backscattered X-rays creating an X-ray data set. In one embodiment, an X-ray tube, RF electron accelerator or linear electron accelerator can be used to generate ramping X-ray pulses. In the case of an X-ray tube, the typical duration of pulse, in one embodiment, can be about 4 ms, with the energy ramp from about 70 keV to 340 keV. In an alternative embodiment for system with linac accelerator as the X-ray source the pulse duration can be shorter, and the maximum end-point energy can be up to 1 MeV or higher.

In one embodiment X-rays are produced by stopping an electron beam 802, for example from an electron accelerator, in a target 801 and generating Bremsstrahlung photons. The energy distribution is a function of the energy of the input electrons while the intensity of the X-ray beam is a function of the total flux of the electron beam. The energy of the resulting X-ray beam is a distribution of photon energies up to a maximum energy (the end point energy) related to the maximum energy of the input electrons. The output X-ray energy distribution can therefore be controlled by adjusting the energy of the input electron beam, a technique well known to those skilled in the art.

In one embodiment X-ray photons are produced by an electron beam 702 that is accelerated to a very high speed and strikes a target 701. The electrons that make up the beam are emitted from a heated cathode filament 1302. The electrons are then focused and accelerated by an electrical field 1301 towards an angled anode target. The point where the electron beam strikes the target is called the focal spot Most of the kinetic energy contained in the electron beam is converted to heat, but around 1% of the energy is converted into X-ray photons, the excess heat is dissipated via a heat sink. At the focal spot. X-ray photons are emitted in all directions from the target surface. There is a small round window in the X-ray tube directly above the angled target. This window allows the X-ray to exit the tube with little attenuation while maintaining a vacuum seal required for the X-ray tube operation.

The X-ray beam can be spatially limited by using a collimator 208. The collimator absorbs X-rays except for those traveling in the selected direction. In one embodiment the system gathers image data by utilizing a rastering technique with a pencil beam source. As the pencil beam passes over the voxel of interest, the detectors gather data from that voxel. The beam is rastering back and forth until the entire target area has been covered. Differences in absorption and scattering cross sections of the target create the differences in data collected by the detectors, effectively creating the contrast of the image.

A variable energy X-ray source can be generated by other means, for example by synchrotron radiation, like that used in a free electron laser (FEL). To create a FEL, a beam of electrons is accelerated to relativistic velocity. The beam passes through a side to side magnetic field produced by a periodic arrangement of magnets with alternating poles across the beam path. The direction across the beam path is called transverse. This array of magnets is called an undulator or a wiggler, because it forces the electrons in the beam to wiggle transversely along a sinusoidal path about the axis of the undulator.

The transverse acceleration of the electrons across this path results in the generation of photons (synchrotron radiation), which are monochromatic but still incoherent, because the electromagnetic waves from randomly distributed electrons interfere constructively and destructively in time, and the resulting radiation power scales linearly with the number of electrons. The wavelength of the radiation emitted can be readily tuned by adjusting the energy of the electron beam or the magnetic-field strength of the undulators.

The X-ray energies may typically vary over a range of several hundred keV. In one embodiment, the lower energy range is about 140 keV while the upper energy range is 450 keV. Depending on the specific application this range could be expanded, contracted, lowered in energy or increased in energy to best fit the desired application. The advantageous range is to keep the X-ray energies in the range where the dominant interaction in the material is Compton scattering. Too low an energy will result in increased probability for photoelectron absorption of the X-rays, resulting in fewer detected Compton scattered photons. Too high an energy will result in increased probability for pair production, lowering the available Compton scattered photons.

In one embodiment, the X-ray source for the proposed system is the one based on the X- or S-band linac with a magnetic scan system, where the electron beam is scanned along the straight path and placed on individually collimated transmission-type X-ray converters. The motion and the dynamic focusing of the electron beam is performed by the magnets, whose strength is dynamically adjusted to account for the changes in the deflection angle, focal distance and the kinetic energy of the electron beam.

Figure 1:
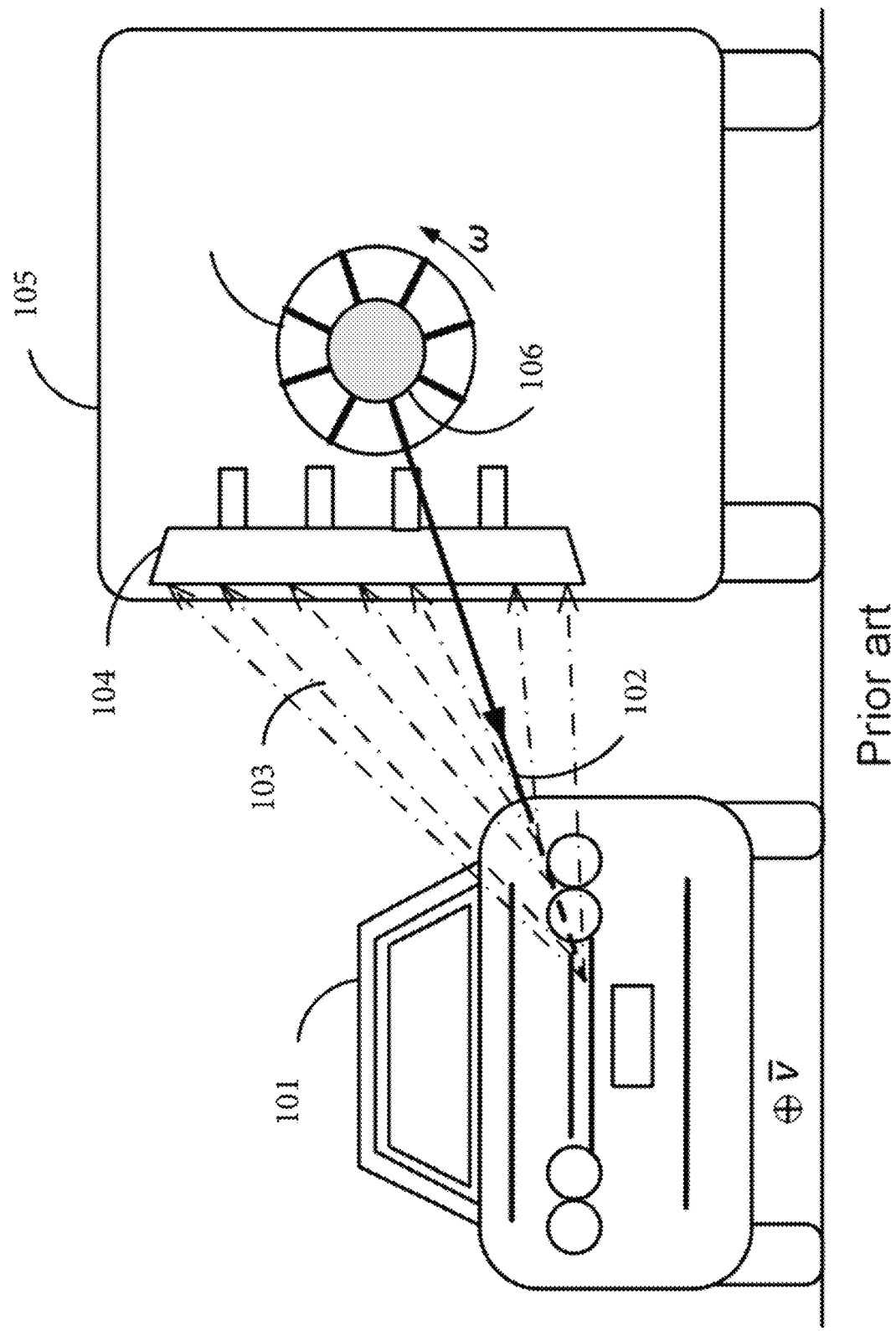
FIG. 1. Prior Art. Illustration of conventional X-ray backscatter cargo imaging system. The X-ray pencil beam is created by the rotating collimator on the right, and is scanned vertically while the object being inspected moves horizontally. The X-ray beam itself passes between two large backscatter detectors, and scattered X-rays are collected and registered at each beam position.
Figure 3:
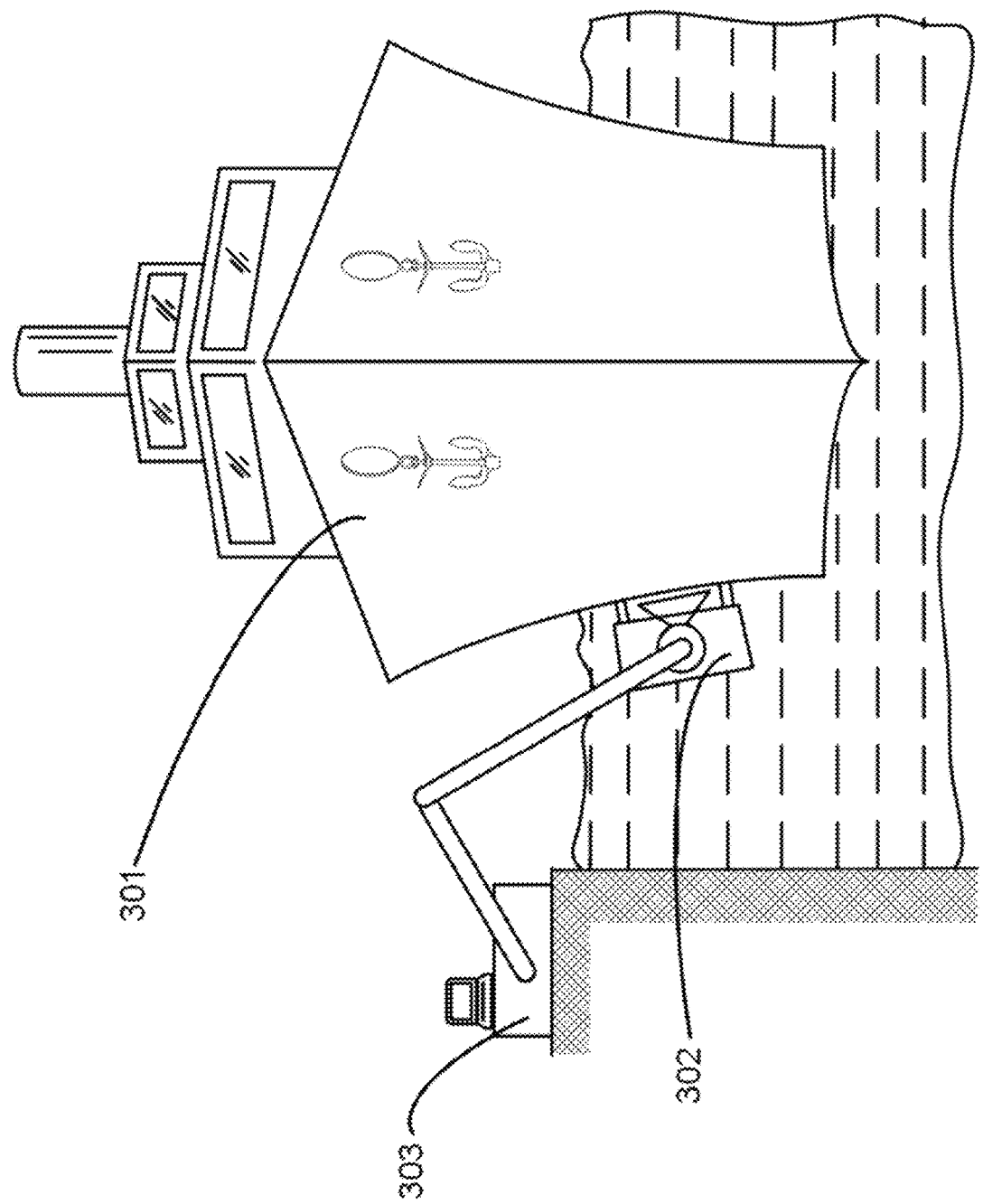
FIG. 3. Artistic view of the X-ray backscatter system for inspection of small ships.
Figure 4:
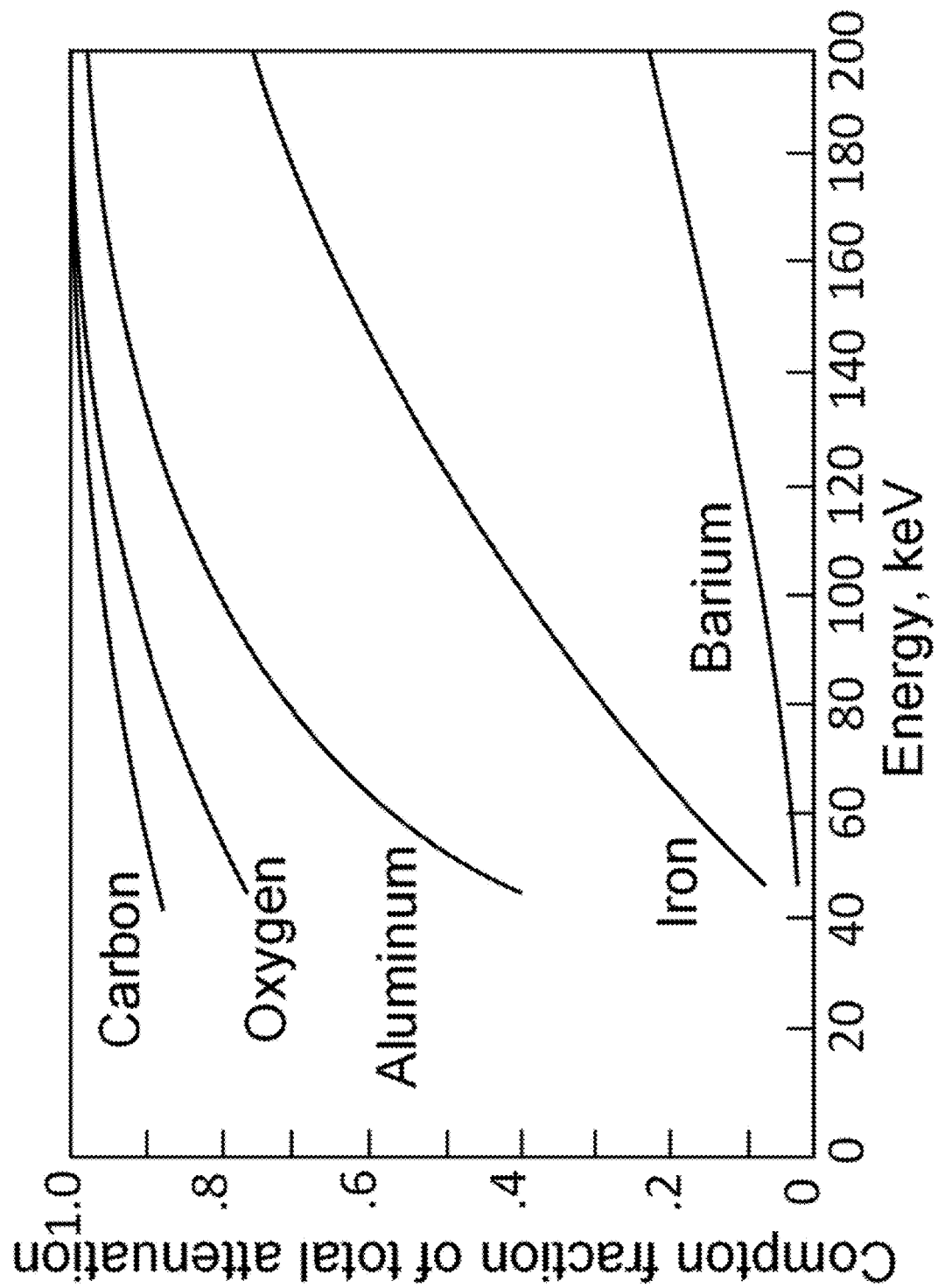
FIG. 4. Fraction of Compton scatter in the total X-ray attenuation as a function of energy for selected elements.
Figure 5:
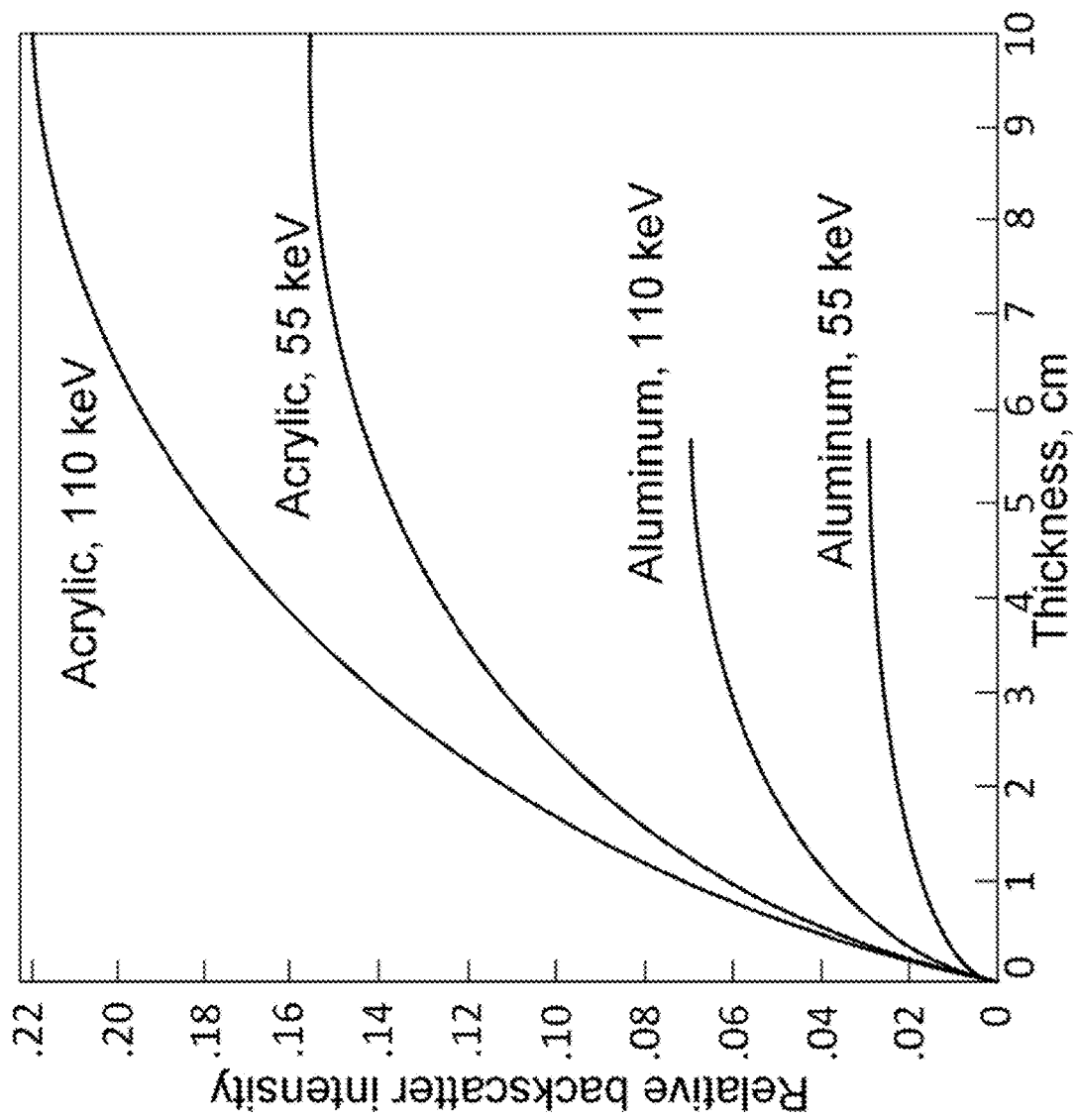
FIG. 5. Calculated backscatter as a function of acrylic and aluminum thickness at 55 keV and 110 keV.

With the scanning pencil beam method, backscatter images are created by raster-scanning a collimated beam of X-rays over the object to be inspected. This is usually achieved by creating a beam that scans in the vertical direction while the object being inspected moves horizontally 109 past the imaging system, FIG. 1 and FIG. 2. Alternatively, the imaging system comprising unit with X-ray generator 302 and position control and DAQ module 303 can move past a stationary object 301, in this case a small ship, that is being inspected. FIG. 3. Specialized mechanical configurations are also available which can scan the pencil beam in two dimensions, so that neither the object or nor the imaging system needs to move during the inspection process. However, the first scanning mechanism is the most commonly used.

The scanning pencil beam is formed by selecting rays from a fixed fan beam by means of a rotating collimator 106, 108, also called a chopper wheel. The rotating collimator is usually preferred over one involving reciprocating motion due to its mechanical simplicity and robustness. The number of spokes in the chopper wheel is selected such that the X-ray source field of view is consistent with the size of objects being scanned, and the angular spread of the X-ray beam. Typical scan speed is of the order of a few to tens of milliseconds per line. The chopper wheel rotation speed is from hundreds to thousands of rotations per minute, chosen as a tradeoff between the image quality and how fast an object is inspected. Spatial resolution of the system is dominated by the diameter of the X-ray pencil beam where the beam intersects the object under investigation. Beam size is determined by the configuration of the X-ray tube focal spot size, chopper wheel aperture, and the distance to the object:

Within the X-ray tube, the electron focal spot size plays an essential role in what type of beam collimation geometry is feasible for a given resolution requirement. Typically, a beam of electrons 802 inside the tube impinges on a high atomic number target (usually tungsten) 801, FIG. 8. In the electron beam—tungsten target collision process, X-rays are emitted in all directions. The target is shielded everywhere except for a small collimator with an aperture 805 placed at the end. Because the area of the tungsten target hit by electrons (focal spot) has a finite size, the beam spot size is determined not only by the aperture position and size, but also by the relative sizes of the focal spot and aperture. The resulting beam spot is substantially larger than if the focal spot had been approximated as a point source An X-ray detector is configured to measure said secondary X-rays that have been backward scattered from the object. The detector may comprise several discrete sensors multiplexed to a computer or the like for simultaneous measurement of the X-ray flux and recording of the position at which it was detected. Alternatively, the detector could be an X-ray semiconductor detector or alternatively a scintillator detector with a photomultiplier readout or alternatively a scintillator with solid-state photo detectors or other such X-ray detectors capable of measuring X-ray flux. Such detectors, together with suitable signal processing and data recording elements, are thus capable of simultaneously measuring the flux of the Compton scattered photons and detecting its position. The image may be provided on a display.

Compton X-ray backscatter Images are formed by scanning a pencil-shaped beam of X-rays along one dimension of an object that is being inspected. At each position of the scanning pencil beam, scattered X-rays are collected by large detectors placed on the same side of the system as is the X-ray source. By tracking the beam's instantaneous position on the object, and measuring the instantaneous intensity of the scattered X-rays that are incident on the detectors, one can associate a scattered intensity to each beam position on the examined voxel of the object.

Figure 14:
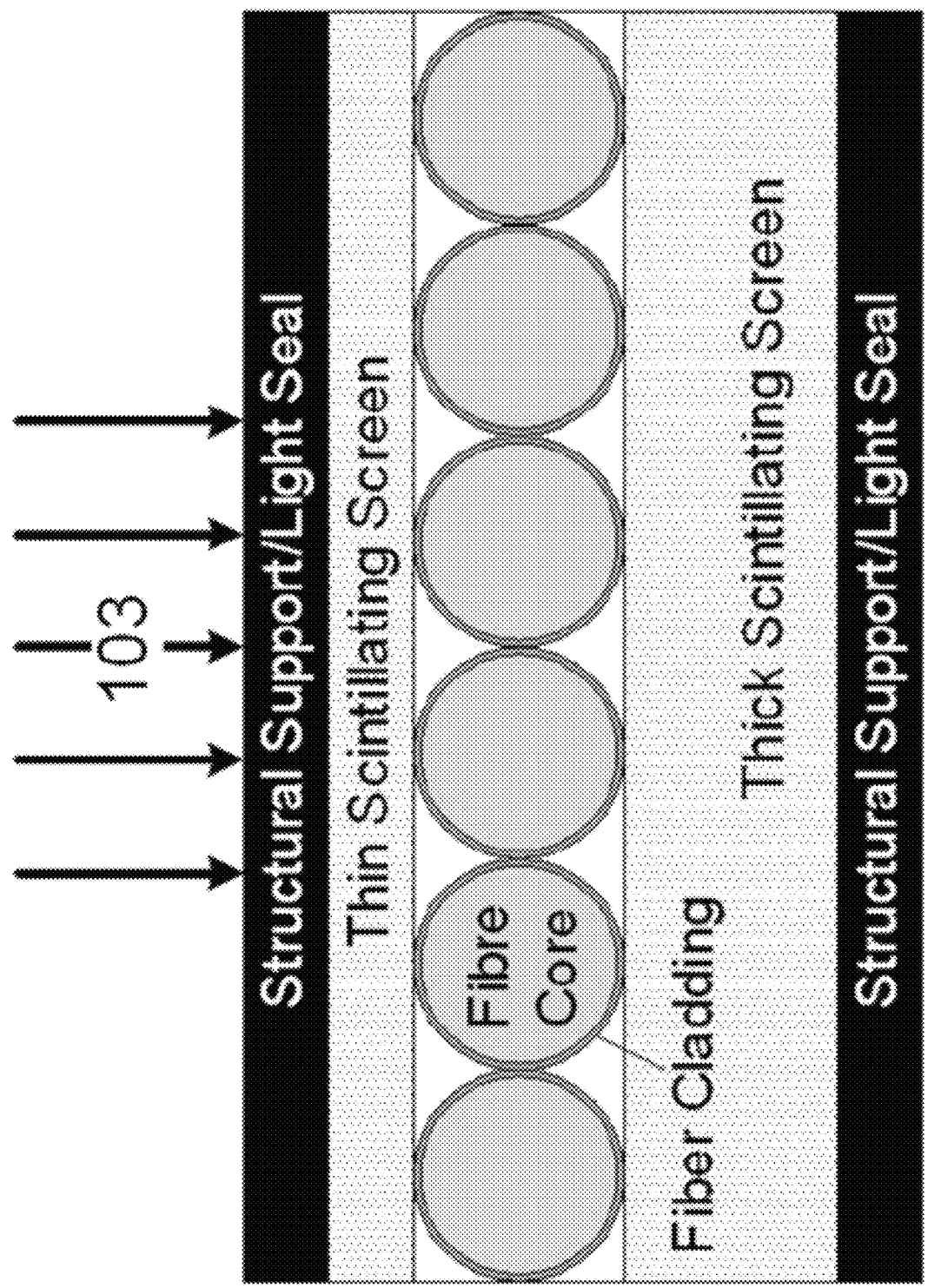
FIG. 14. Cross section of BaFCl(Eu) scintillation detector with WSF readout.

Depend of application, there are different X-ray generators and beam scanning methods can be used. For the systems with energy up to 360 keV, generator based on AC triode X-ray tube is suitable. For MeV systems, proper will be sub-MeV electron linac with single-gap RF cavity. FIG. 14.

In Compton X-ray backscatter systems, the maximum energy of photons arriving to detectors is below 300 keV, irrespective of the energy of primary photons. Therefore, to achieve acceptable stopping power, the areal density of detectors doesn't need to be high.

In a typical backscatter X-ray imaging system, an X-ray pencil beam scans an imaged target in a linear motion, while elongated radiation detectors are arranged on both sides of an exit aperture of an X-ray source. As the pencil beam moves, the detector area closest to the beam will typically receive the strongest signal and detector area further from the beam less. If the detector area is segmented into individually readable sections (tiles) the signal to noise ratio of the detection system can be improved by only reading the segments with a good signal to noise ratio and neglecting the segments which would contribute predominantly noise to the summed signal. The selection of contributing detector segments can be made based on the actually detected signal or based on the known position of the pencil beam.

The choice of specification for the pencil beam depend on the desired spatial resolution of the inspection system usually in trade between improved spatial resolution at the cost of lower X-Ray flux on the object. The use of the term "pencil beam" herein is used to indicate that characteristic X-ray beam dimensions and divergence desirable for each imaging situation. The beam shape, dimensions and divergence are parameters chosen for the specific imaging situation. Different combinations of these beam properties are included under the general term "pencil beam" with the common characteristic that the beam has generally low divergence. The pencil beam specifications are important in defining the imaging resolution of the system.

Two exemplary basic designs of detector considered for proposed backscatter inspection method with energy- and current-modulated pulses. First Is scintillation detectors based on dicilicate of barium ($BaO_2$—$SiO_2$) glass doped with Cerium (DSB:Ce), which has previously been described in E. Auffray et al. "DSB:Ce3+ scintillation glass for future," journal of Physics: Conference Series, 587 (2015) 012062. DOI: 10.1088/1742-6596/587/1/012062, which is incorporated herein by reference. A second one consist of multilayered BaFCl(Eu) scintillation sheets sandwiching with wave-shifting fibers (WSF) which has previously been described in A. Arodzero, J. Callerame, D. Dinca, R. Sud, L. Grodzins, M. Rommel, P. Rothschild, J. Schubert, X-ray inspection using wavelength-shifting fiber-coupled scintillation detectors, U.S. Pat. No. 9,285,488 which is incorporated herein by reference. Silicon Photomultipliers (SiPM) can be used for readout of both proposed detectors.

In one embodiment, the Compton scattered X-rays are detected by an array of fast detectors generating a detection signal in high Z crystals that allow for a highly efficient and compact detector array. Each pixel of the array is read-out by SiPM and signals are processed in the detector electronics. The SiPMs are fast photodetectors allowing photon number (integrated flux) and temporal resolution. In some embodiments, the fast high Z detector materials used are scintillation detectors. SiPMs provide the needed gain and sensitivity to adequately utilize these detector materials.

A major factor in the quality of the backscatter image is the number of photons used to create each pixel. The fewer photons forming each pixel, the more statistical variations will be visible in the signals from one pixel to the next. This statistical noise is the source of the grainy appearance of X-ray images. Images produced with higher flux sources, or using longer periods of time to accumulate more photons, will have a smoother appearance than faster or lower flux images. The statistical quality of the image also indirectly influences other facets of quality such as resolution and penetration. The number of photons produced by an X-ray source is proportional to the current (mA) and accelerating voltage (kV) of the beam of electrons incident on the production target. The X-rays produced have a broad energy spectrum with the maximum being equal to the maximum energy of the electrons that produced the X-ray photons via Bremsstrahlung. The relationship between photon flux and mA is linear, while the relationship with kV depends on a number of factors.

The selection of X-ray tube voltage is determined by the object scanned and the degree of penetration required. To image objects behind metallic sheets with thicknesses of a few millimeters, a higher energy is desirable. Voltages are typically up to 300 kV, with currents from 3 to 15 mA. Such a tube requires radiation shielding, a collimation mechanism. a high voltage power supply and associated cooling. The X-rays need to travel into the container wall, scatter from the contents of the container and then travel back to the detectors. Regardless of the energy of the incident X-ray photons, the X-rays scattered at 180 degrees (backscattered) can have a maximum energy of 255.5 keV (half of the rest mass of the electron expressed in keV). Even if the impinging X-rays can reach deep into the cargo container, the scattered photons may be absorbed on their way back because of their low energy.

The detection requirements for proposed system are different from the requirements addressed by detectors used in existing backscatter inspection systems. In addition to large sensitive area, detectors will preferably have position resolution. In one embodiment, the detector array would be tiled. Further considerations for the detector are good stopping power in extended energy range, and ability to provide time resoling within X-ray pulse. In one embodiment, a detector based on wavelength-shifting fiber-coupled scintillator can meet these preferred criteria.

How bright an element appears to be in an X-ray backscatter image is not a function of the Compton cross section alone. The interplay between the Compton interaction probability (cross section), the probability of photo-absorption, material thickness and density, and X-ray fluorescence contribute significantly to the end result.

In one embodiment, the X-ray source is ramped from low to high energy. The Compton scattered flux is recorded for this energy ramp using fast detectors with timing capabilities to produce data from each energy bin along the energy ramp. Alternatively, in an embodiment the energy can be ramped down in energy, from high to low with data recorded during the ramp down. Likewise, the Compton scattered flux is recoded for each energy corresponding to the energy ramp. In a further embodiment, the energy ramping can go from low to high then high to low in a continuous or semi-continuous matter with Compton scatter flux recorded by the detectors accordingly.

It is possible to access the electron density $\rho x$ of each material layer 806, 807 by monotonically increasing the end-point-energy, $E_f$. The thickness of each layer is chosen based on the penetration of the backscattered X-ray beam determined by the electron beam energy of the source. The penetration thickness is defined as thickness that stops 99% of all backscatter flux from reaching the detector. The X-ray source illuminates the object with a first set of X-rays and the X-ray detector measures the integrated flux of backscattered X-rays creating a first X-ray data set. A lookup table is used to estimate the material attenuation coefficients (E) and $\mu(E')$ for the first layer. The X-ray energy is increased to reach a second material layer. Then calculate $\rho x$ of the second layer and use the lookup table to estimate the material attenuation coefficients (E) and $\mu(E')$ for the second layer. The X-ray energy can be repeatedly increased to iterate this layer pealing process.

The values held within the lookup table are determined from experimental measurements for X-rays at different energies and for the various different materials.

An ordinary dedicated computer or processor equipped with input output capability and data storage is used to process the data. Algorithmically, the "peeling" of multiple layers in the X-ray backscatter is done following these steps:

1. Start with the end-point-energy which provides information about the first material layer
2. Measure $\rho x$ of the first layer
3. Using lookup table estimate material attenuation coefficients (E) and (E') for the first layer
4. Increase the electron beam energy to reach the second layer
5. Calculate $\rho x$ of the second layer using equation 4
6. Using lookup table estimate material attenuation coefficients (E) and $\mu(E')$ for the second layer
7. Repeat steps 4 through 6 for subsequent layer(s)

The computer processor contains a look-up table of possible material attenuation coefficients. In one embodiment calculations were based on NIST material attenuation values and nominal X-ray spectrum. In one embodiment the initial Bremsstrahlung spectrum is generated by 200 micron Tungsten transmission-type X-ray converter 801. The resulting X-ray flux is transmitted to targets of 1 mm steel, 1 cm aluminum, 6 cm polycarbonate and 10 cm polycarbonate 806, 807. For each target the backscatter flux into a 170° ring detector is calculated using Klein-Nishina formula. Both forward and backscattered flux is attenuated by the material thickness in their respective paths.

The proposed method bases on the idea that both penetration and backscatter flux increase with the end-point energy of the X-ray beam. Assuming nearly perfectly perpendicular geometry, the total X-ray backscatter signal in an energy integrating detector produced by the cargo with thickness dx at the depth of x can be expressed as:

$$I(E_f) = \iint E'(E,\theta) I_0(E) \sigma_{KN}(E,\theta) \rho_e dE (e^{-(\mu(E)+\mu(E'))x}) dx \quad \text{(Equation 1)}$$

where $I_0$ is the initial flux, $E_f$ is the end-point-energy of the X-ray flux, $\sigma_{KN}(E, \theta)$ is the Klein-Nishina cross section for initial energy E and the detector angle $\theta$, $\rho$ is the areal electron density and $\mu(E)$ is the material attenuation. The scattered energy E' is expressed as $$E' = \frac{E}{1 + \frac{E}{m_e c^2}(1 - \cos\theta)} \quad \text{(Equation 2)}$$

Equation 1 can be approximately re-written in a discrete form as $$I(E_f) \approx \int^{E_f} E'(E,\theta) I_0(E) \sigma_{KN}(E,\theta) dE \sum_{j=1} \rho_j x_j [\Pi_{i<j} e^{-(\mu_i(E)+\mu_i(E'))x_i}]. \quad \text{(Equation 3)}$$

where $\rho_j$ is the areal electron density in the layer j and $x_j$ is the thickness of the layer j. Using Equation 3 the electron density can be expressed as $$\rho_j x_j = \frac{I(E_f)}{\int^{E_f} E'(E,\theta) I_0(E) \sigma_{KN}(E,\theta) dE} - \sum_{i<j} \rho_j x_j \left[ \prod_{i<j} e^{-(\mu_i(E)+\mu_i(E'))x_i} \right] \quad \text{(Equation 4)}$$

The electron density $\rho_j x_j$ of each material layer is determined by monotonically increasing the end-point-energy, $E_f$. The thickness of each layer is chosen based on the penetration of the backscattered X-ray beam determined by the electron beam energy of the source. The penetration thickness is defined as thickness that stops 99% of all backscatter flux from reaching the detector.

In one embodiment, the following items are employed:
Only backscatter is tallied in the detector,
All backscatter signals are normalized by the forward X-ray flux,
Near constant backscatter signal from the front layer,
Subtracting the signal at low energy (<150 keV) from high energy signal (>350 keV) allows access to the second layer contribution to the total signal,
Subtracting the signal at energy about 250 keV from high energy signal (>350 keV) allows access to the contribution of third layer,
Near constant backscatter signal from the front layer,
Possibility to identify first, second and third layer material.

In one embodiment for a two-layer scenario the imaging process may proceed as follows:
1. Record temporal profile of backscatter detector response to X-ray pulse (detector pixel data).
2. Divide detector pixel data Into low and high energy components.
3. Estimate from the slope of the backscatter signal the areal electron density of material of second layer.
4. Subtract weighted low energy signal from high energy signal.
5. Record image pixel signal value.
6. Repeat steps 1-5 for all beam positions within scan line.
7. Transmit line image pixel signals to segmentation algorithm.
8. Calculate color and saturation for color-coded backscatter image.
9. Render "behind the wall" image.

In regard to a three-layer scenario the algorithm is similar to the above. To calculate the parameters of the third layer the value of the second inclined portion of detector pixel data is used. Segmentation of the image may be accomplished by standard algorithms such as that presented in C. Zhi-qiang et al., A Curve-based Material Recognition Method in MeV Dual-energy X-ray Imaging System, Nucl. Sci. Tech. 27 (2016) no. 1, 25 (2016). DOI: 10.1007/s41365-016-0019-4, which is incorporated herein by reference.

At high energies, the backscatter starts to be dominated by the material attenuation of the backscattered flux ((E) term in eq. (1)) due to the maximum backscatter X-ray energy being limited to the half of the electron rest mass. The attenuation length in all materials increases a function of energy below ~600 keV at which point the flux is expected to remain constant. However, within this range, the backscatter penetration, particularly in steel, varies sufficiently strongly to allow separation of multiple layers by changing end-point energy. For example, in a two-layer system with organic cargo behind steel container wall, the backscatter signal generated with low energy X-ray beam will be dominated by the scattering from container wall, whereas a larger fraction of higher energy X-ray beam interrogates the cargo behind the initial steel layer.

Figure 6:
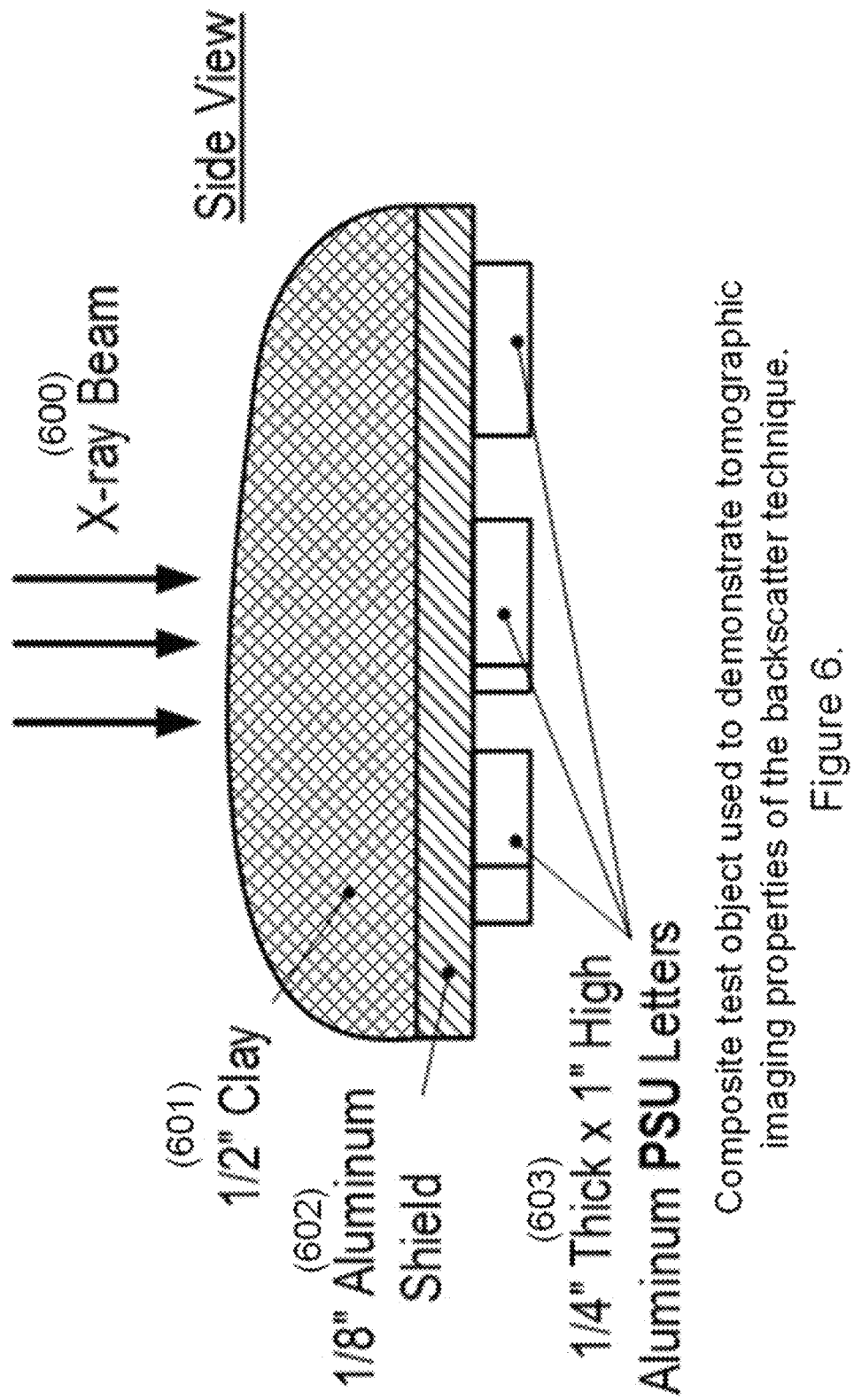
FIG. 6. Composite test object used to demonstrate tomographic imaging properties of the backscatter technique.
Figure 7:
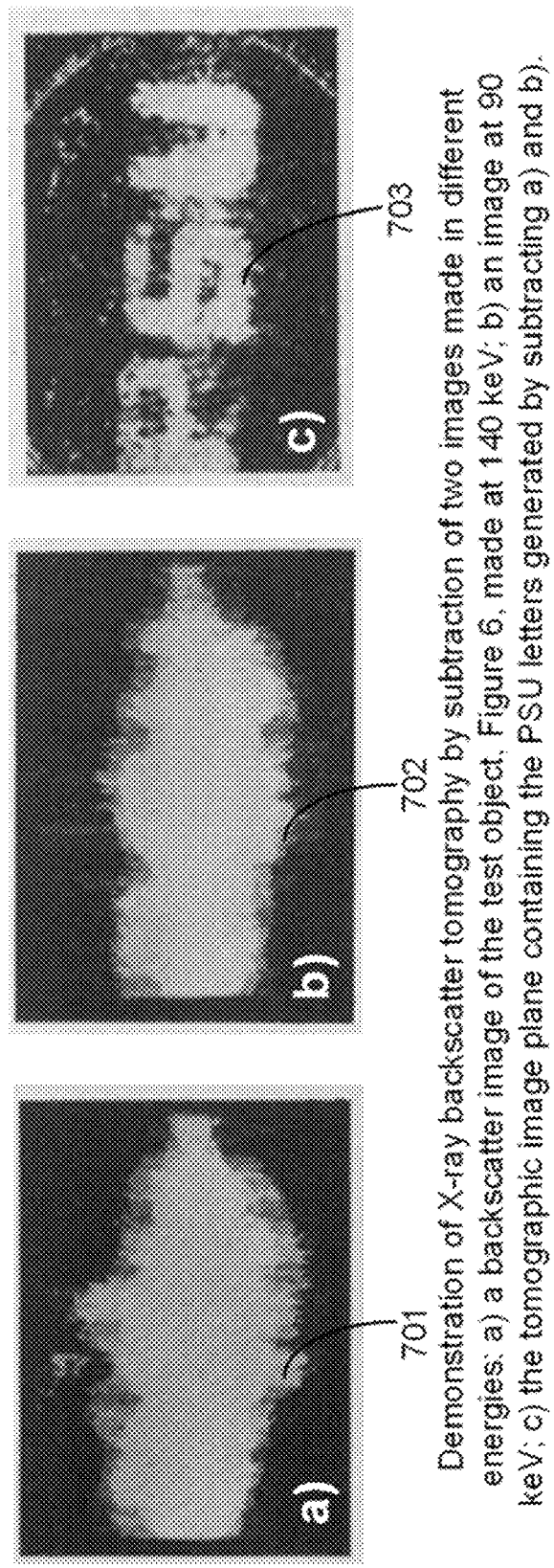
FIG. 7. Demonstration of X-ray backscatter tomography by subtraction of two images made at different energies. a) is a backscatter Image of the test object made at 40 keV, b) an image at 90 keV, and c) shows the tomographic image plane containing the PSU letters generation by subtracting a) and b).

Previously a dual energy method was employed where two carefully chosen energies 604 are used to resolve aluminum 602, 603 image behind the clay layer 601, FIG. 6 and FIG. 7. This has been described in B. Towe, A. Jacobs. X-ray Backscatter Imaging, IEEE Transactions on Biomedical Engineering, Vol. BME-28, 9, 1981, pp. 646-654, which is incorporate herein by reference. The instant disclosure expands on this approach by using multiple energy ranges and adaptively selected energies to image multiple layers of cargo. This instant method does not know a priori the content of the cargo and thus instead of preselecting X-ray energies it adaptively choose the energy ranges a posteriori based on the cumulative backscatter signal.

MCNP Simulations

Figure 8:
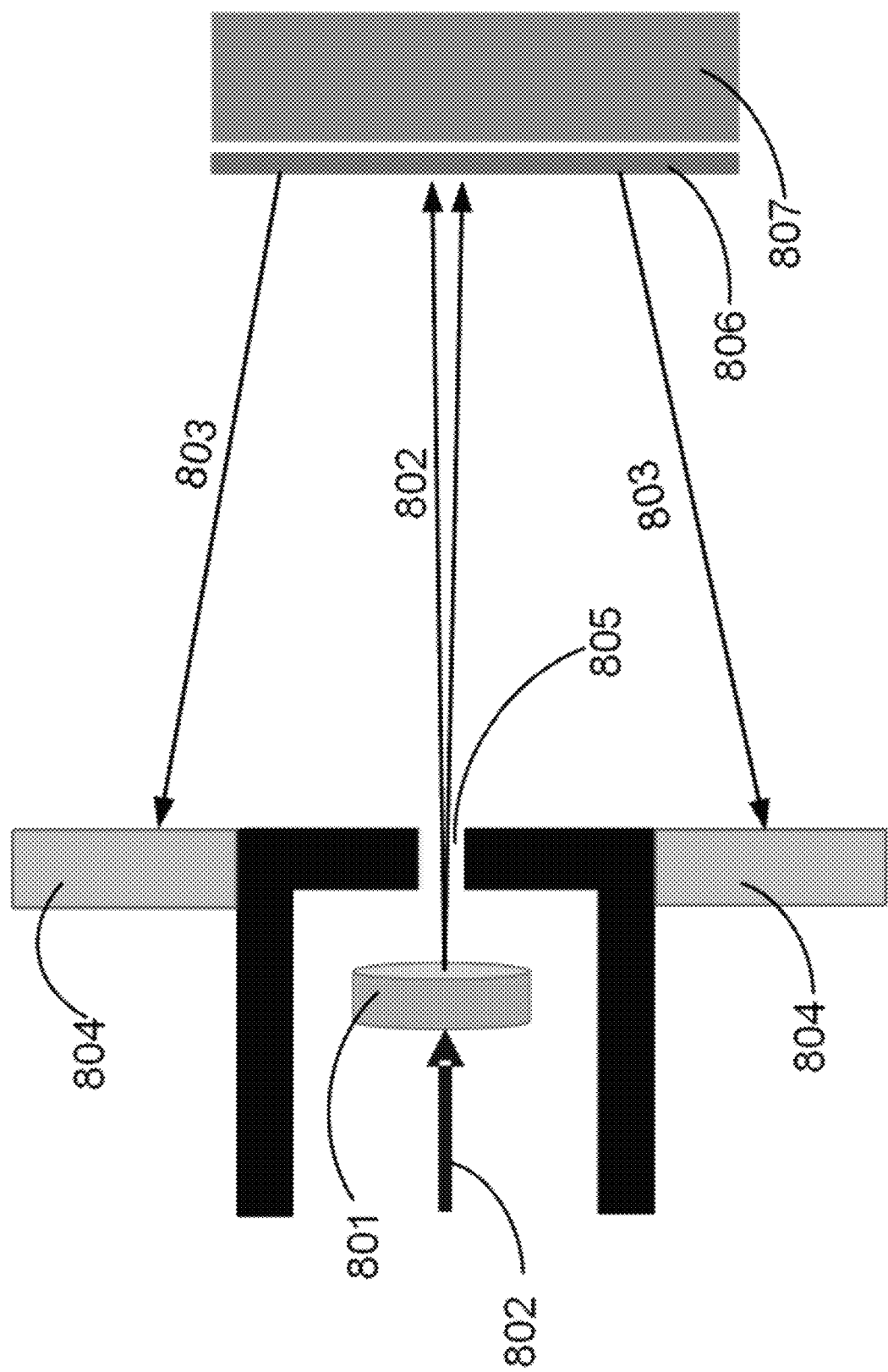
FIG. 8. MSNP simulation model.

To demonstrate the feasibility of separating multiple cargo layers using X-ray beam with multiple end-point energies, we present MCNP6 based simulation studies for two and three layer cargoes. FIG. 8 schematically shows the simulation geometry. The electron beam with energies between 50 keV and 1.5 MeV hits the 200 m transmission type Tungsten converter. The resulting X-rays illuminate the cargo consisting of uniform layers of material.

Figure 9:
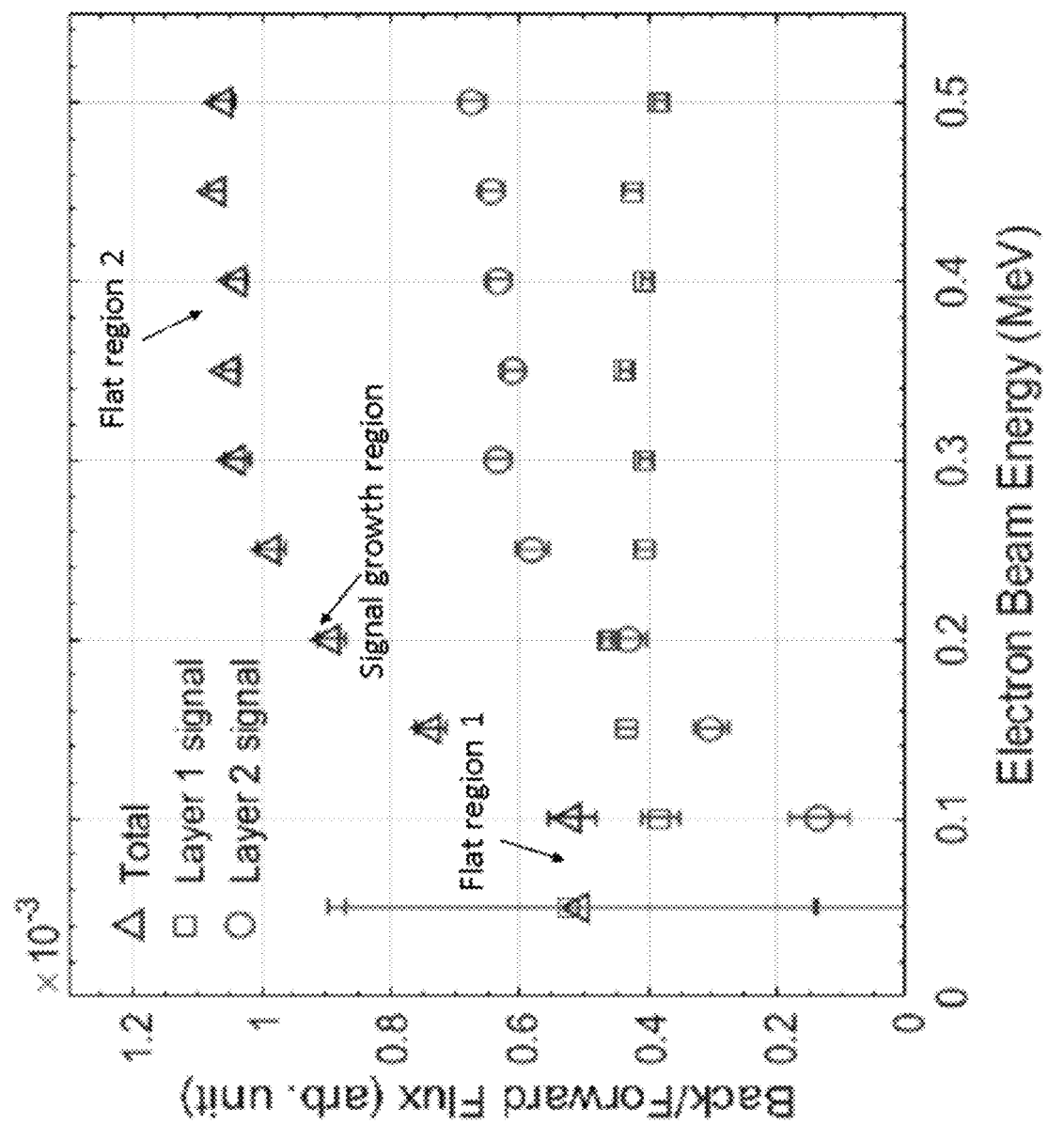
FIG. 9. Steel shipping container simulation data.

FIG. 9 shows the results of the simulations for a cargo container composed of 2 mm thick layer of steel (container wall) and 2 cm of A-150 tissue-equivalent plastic material (cargo, density of 1.1 g/cm$^3$). The total signal at low energy, <150 keV, is dominated by the backscatter signal from the first layer, which remains nearly constant over the full energy range, whereas the backscatter signal from the second layer starts to dominate above 300 keV.

This result demonstrates a method for separately Imaging the first and second layer. The total backscatter signal is acquired for each detector pixel, and two-layer imaging signal is broken up into the flat region at low energy, region of growing signal and finally the flat region at high energy. The first region provides the first layer signal, whereas the difference between plateaus in the third and first region provides a signal from the second layer. The location and duration of these regions depend on the thicknesses of each layer. Therefore, the main advantage of this method over a fixed or dual energy system is the ability to determine the location of these regions by scanning across a wide range of electron beam energies. The figure shows that a 250 keV X-ray source typically used in a backscatter imaging systems is insufficient to separate a signal from the container wall from the organic cargo inside.

Figure 10:
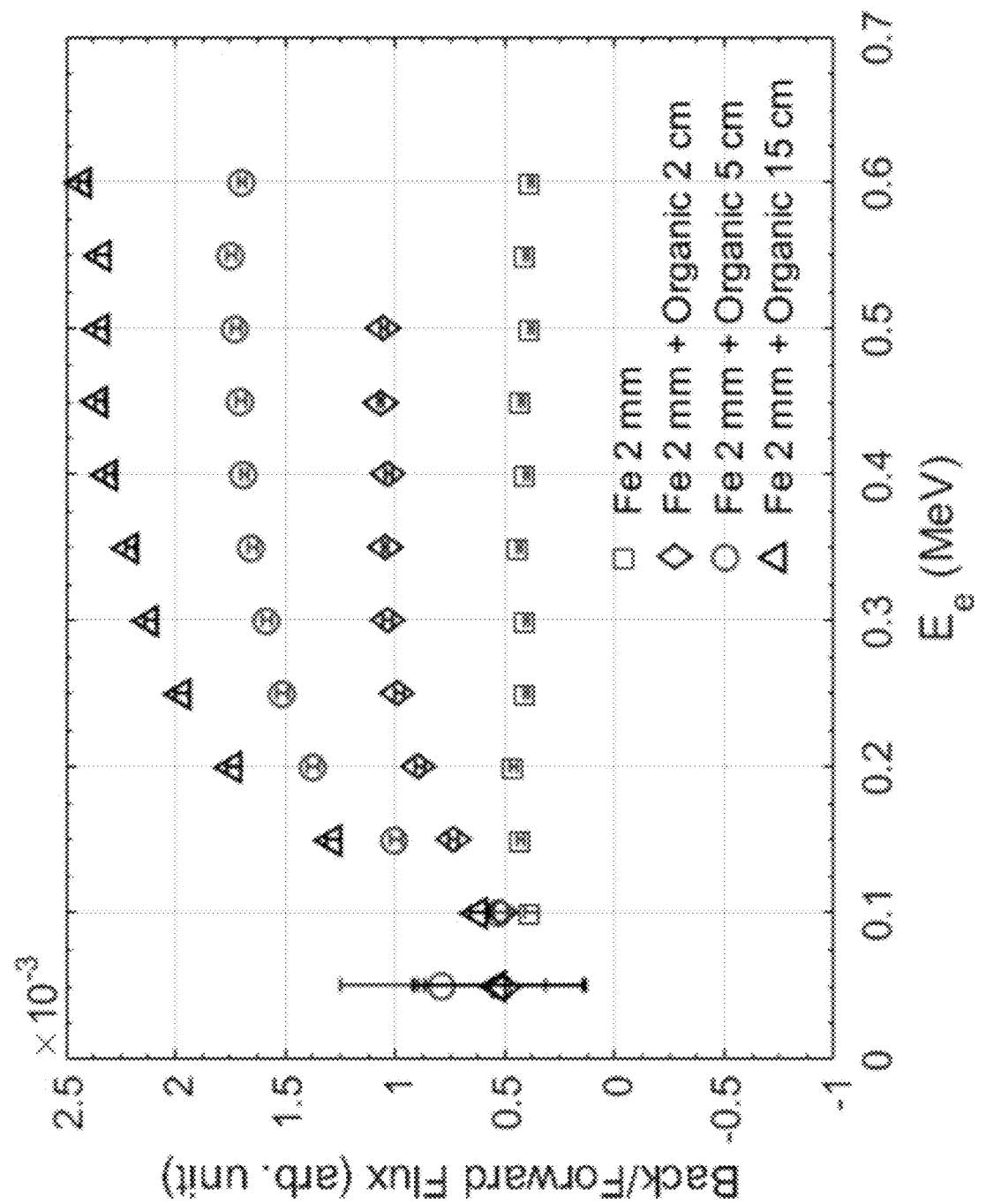
FIG. 10. Simulation data for boat in water.

The ability to image the second layer requires the backscatter signal from this layer to vary as a function of its thickness. In FIG. 10 we demonstrate a capacity to image the second layer by varying the thickness of the organic cargo behind constant thickness of steel container wall. The backscatter signal increases proportionally to the thickness of the organic cargo behind the steel wall. Moreover, all thicknesses show the same signal profile as a function of the end-point energy, which allows applying the same layer reconstruction procedure to a wide range of thicknesses.

As the pencil beam moves across the surface of an interrogated object, the signal in the flat region represents the image of the second layer.

Figure 11:
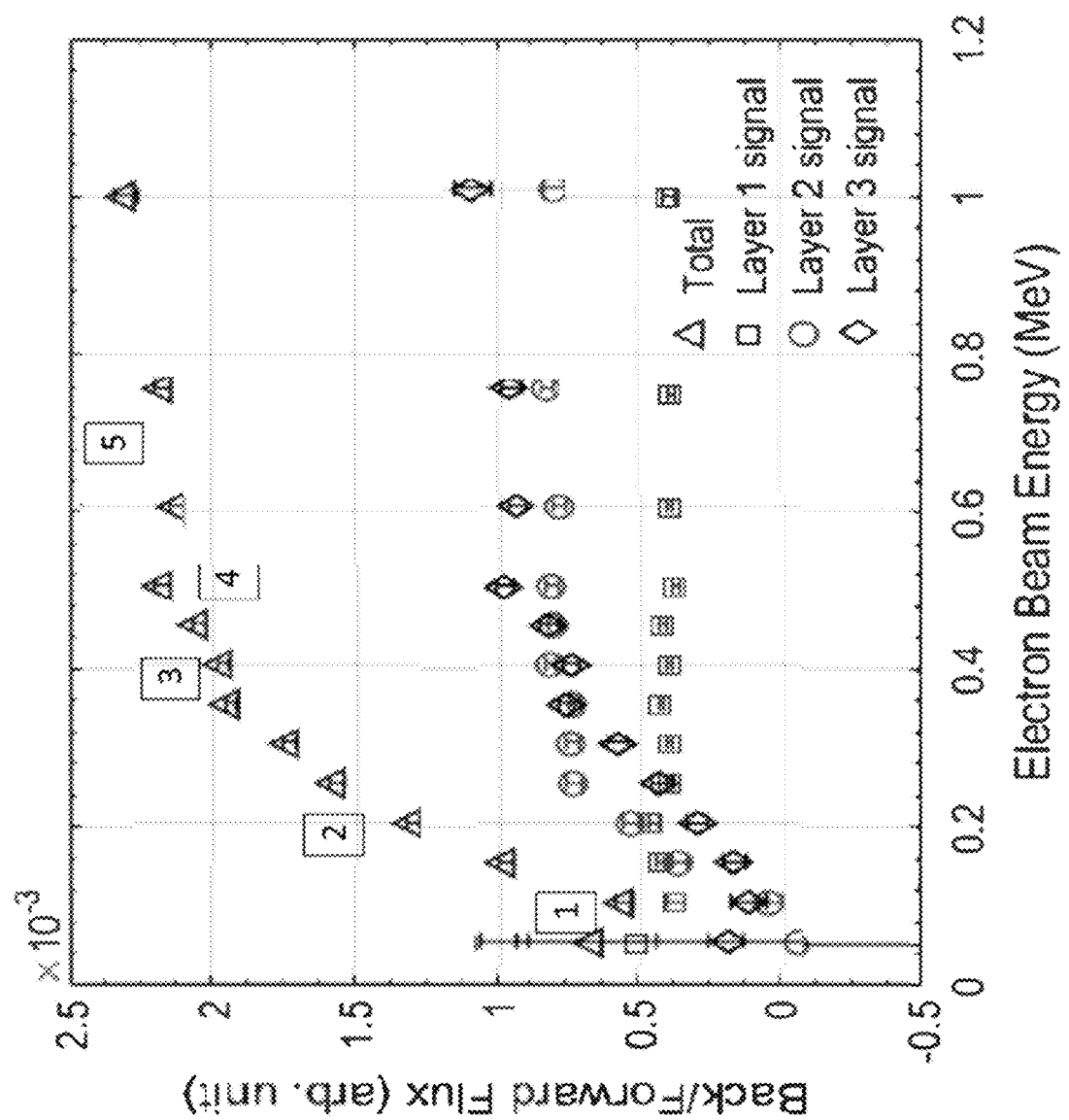
FIG. 11. Simulation data for air container.

Simulations also indicate that for some thicknesses and types of cargo there exists a possibility to apply the same method in order to separate three layers of cargo. The results of the simulations with 2 mm of steel followed by the combination of 2.5 cm of organic cargo and 2 cm of steel are shown in FIG. 11.

The total signal consists of three flat regions corresponding to three layers of the cargo material, with each layer dominating the total signal. The flat regions are separated by regions where the backscatter signal increases, corresponding to at least two layers contributing to the total signal. The three-layer separation is much more difficult and requires good control of hardware systematics and data statistics. The range of thicknesses in which the organic layer is clearly separable from steel layer behind it is limited, ~2.5±0.5 mm. The range is a good fit for a maritime application of X-ray scanning of cargo ship hauls the concept for which is shown in FIG. 3.

In this maritime application, the length of the water column between the X-rays source and the ship can be accounted for in order to optimize the imaging of the objects behind the ship wall (third layer). In this case, the backscatter signal from water is similar to the simulated organic material. Our simulations show that two- and for some cases three-layer reconstruction is feasible in the X-ray backscatter systems when the end-point energy of the X-ray beam is scanned in a predictable fashion.

X-Ray Backscatter Detectors

In Compton X-ray backscatter systems, with backscatter angles approaching 180 degrees, the maximum energy of photons arriving at detectors is below 300 keV, irrespective of the energy of primary photons. Therefore, an adequate stopping power can be achieved with relatively low areal density detector materials.

In a typical backscatter X-ray inspection system the detector spatial resolution is of no concern at all, since the resolution is governed by the incident pencil beam rather than by detector. In such systems, an X-ray pencil beam scans an imaged target in a linear motion, while elongated radiation detectors are placed on both sides of an exit aperture of an X-ray source. Conventional backscatter detectors is typically designed as a light-tight box lined with scintillating screens where incident X-ray radiation is converted into scintillation light. Large-area photomultiplier tubes are coupled to receive scintillation light via portholes. Due to light absorption in scintillation screen and multiple reflection losses, the light collection efficiency of such detector is inherently low, with only a few percent of the generated scintillation light collected into the photomultipliers.

A better sensitivity and light collection efficiency is achieved with the thinner detector design considered for the proposed backscatter inspection method as was previously described in X-ray inspection using wavelength-shifting fiber-coupled scintillation detectors, U.S. Pat. No. 9,285,488, which is incorporate herein by reference. It consists of multi-layered BaFCl:Eu scintillation sheets sandwiching with wave-shifting fibers (WSF). Upon incidence of X-ray photons, scintillation light emitted by scintillating screen is coupled via cladding into core of the respective fibers, downshifted in frequency (i.e., red-shifted) and propagated to photodetectors. SiPM can be used as a readout photodetectors. This detector design enables the construction of relatively thin large-area backscatter detectors.

For systems with an accelerator where the pulse duration is several microseconds, a suitable detector material is disilicate-barium glass activated with cerium:DSB:$Ce^{3+}$, which has been previously described in E. Auffray et al. "DSB:Ce3+ scintillation glass for future," Journal of Physics: Conference Series, 587 (2015) 01206, DOI: 10.1088/1742-6596/587/1/012062 which is incorporated herein by reference. The principal scintillation decay time for this glass is about 40 nanoseconds. From this glass, it is possible to make tiles for large area detector panels. SiPM also can be used for readout of scintillation signal from the tiles.

As pencil beam moves, the detector area closest to the beam will typically receive the strongest signal. The proposed novel design allows segmenting the detector area into individually readable sections (tiles) resulting in significantly higher signal to noise ratio (SNR). In this concept, the improved SNR is achieved by reading only the segments with strong signal. The selection of contributing detector segments can be made based on the actual detected signal or based on the known position of the pencil beam.

X-Ray Sources

Figure 12:
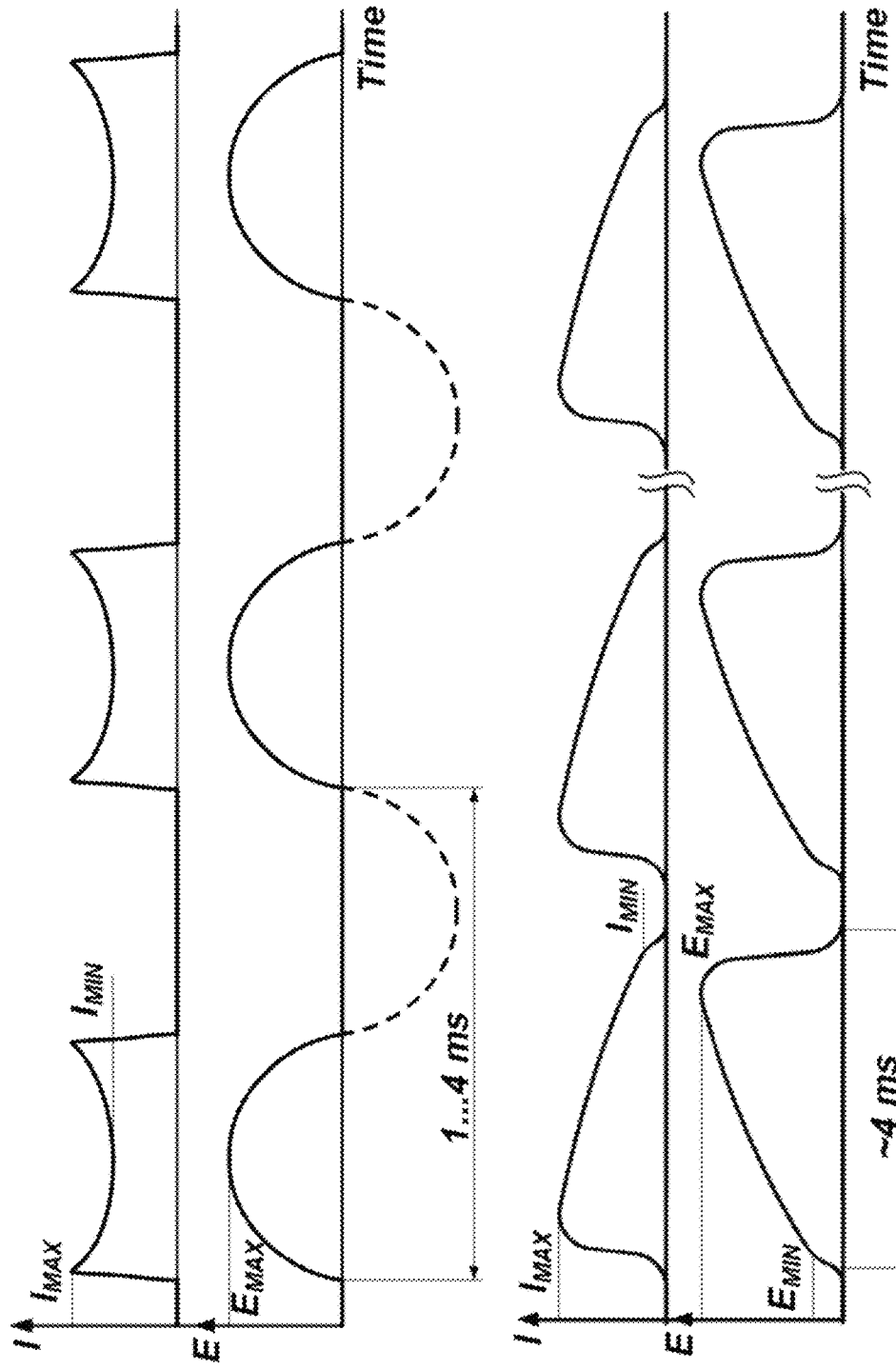
FIG. 12. Exemplary energy and current profiles of X-ray pulses. Top: System with AC triode X-ray tube; Bottom: System with electron linac as an X-ray source. In case of X-ray tube, typical duration of pulse can be about 4 ms, energy ramp can be from ~70 to 340 keV. For system with linac pulse duration will be shorter, maximum end-point energy can be up to 1 MeV or higher.

One component of the proposed system is the X-ray source capable of generating X-ray beam with end-point energies varying in a predetermined and predictable manner. FIG. 12 shows the how a possible X-ray source, either an electrostatic or an RF linac, can generate the required energy and beam current profiles.

Electrostatic X-ray tubes are commercially available and with some modifications can meet the specified performance for the proposed inspection system. However, the tubes with the higher energies (up to 600 keV) are very bulky and expensive. The maximum energies obtained in practical backscatter X-ray tubes are usually below 350 keV. To achieve higher energies, in one embodiment an RF accelerator with sub-MeV energy ramping is used.

In RF accelerator, it is importance to maintain the synchronism between the electromagnetic wave and the particles. If there is a mismatch between their speeds, the phase oscillations will occur. If these oscillations become unstable the particles will be lost. The speed of the electrons depends non-linearly on their energy. For example, at 100 keV it is 54.5% of speed of light, at 500 keV-86.3%, and 94.1% at 1 MeV. The speed of EM wave is defined by the accelerating structure design. When the sub-MeV electron linac with energy ramp is required, its design must either assure stable phase oscillations for the beams in all energy region, or be short enough not to allow the instabilities develop, and prevent the beam from being lost. Multi-cell accelerating structures typically used in industrial linacs for their effectiveness are unable to provide the required performance for all energy regimes from 0.5 to 1.5 MeV. Their efficiency drops dramatically, since the beam velocity profile becomes way too disparate from the wave velocity profile.

Figure 13:
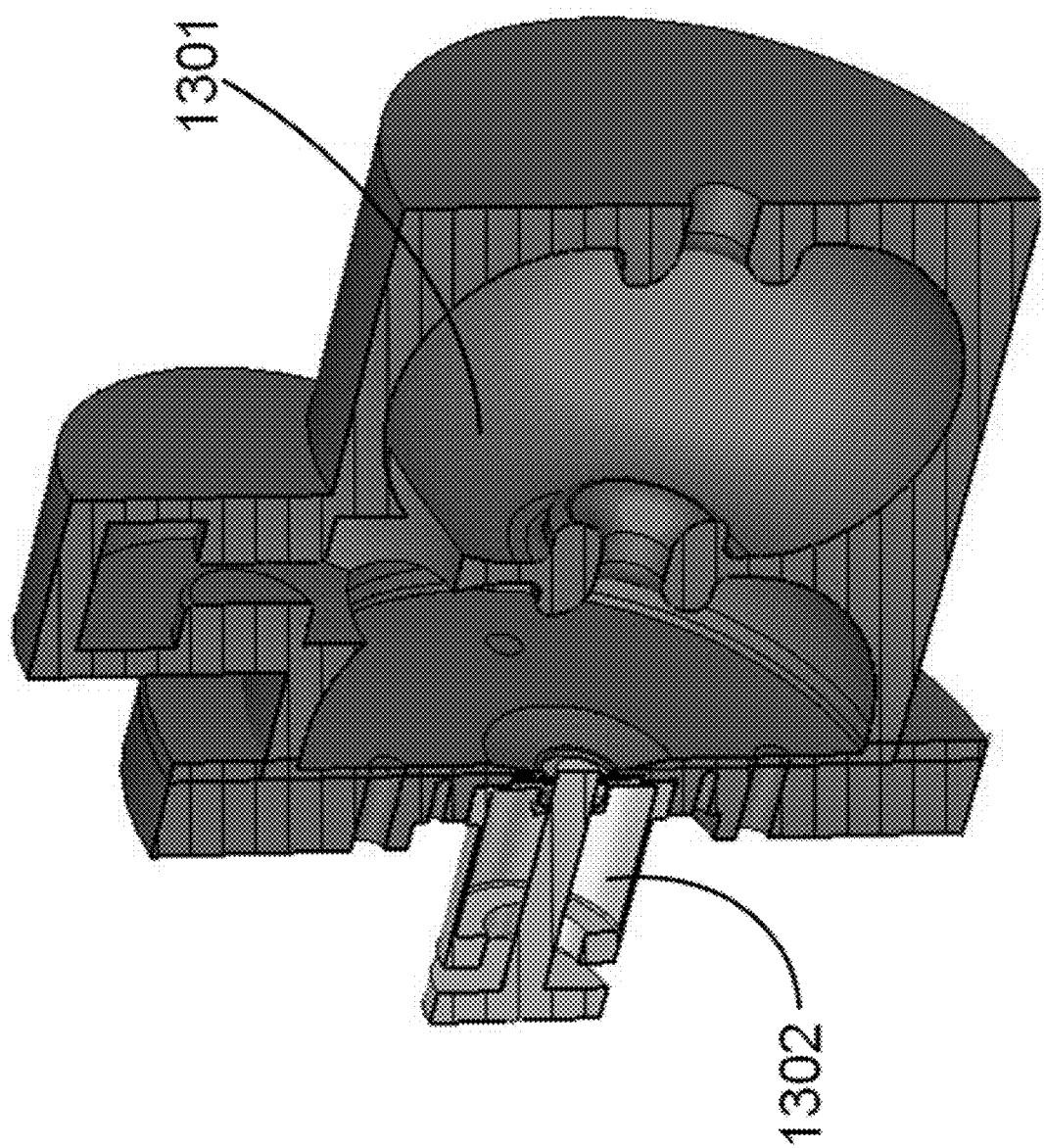
FIG. 13. Principal design of sub-MeV linac with single-gap RF cavity.

Before the electron beam reaches the velocity close to the speed of light (>~1 MeV), where it does not have phase oscillation, it is very vulnerable to the RF field mismatches. We propose to use an RF cavity with 1-2 gaps, FIG. 13, so that the phase oscillations don't develop. In this case, the cathode is attached directly to the cavity. Such an approach is well known, and used in RF electron guns.

The energy ramp in such cavity is achieved by increasing the power from the RF source, that causes the electric field ramp (E~P1/2). Due to the absence of phase oscillations the energy spectrum of a single-cell gun is nearly uniform. By adding more cells, we can compress the spectrum but narrow the linac energy range. A compromise solution can be found depending on the system requirements. Several commercially available RF power sources allow needed rate of RF power change including klystrons, inductive output tubes or solid-state generators.

In one embodiment, the delivery of the pencil X-Ray beam in backscatter systems is enabled by the fast rotating collimator. However, the rotation frequency suitable for the instant technique may not be attainable. In other embodiments, the X-Ray beam delivery is based on the scanned electron beam. The electron beam is scanned on the reflection type of an X-Ray converter by the magnetic deflection system. Each addressable position on the converter is collimated to point a pencil X-ray beam to a unique location in cargo. A fast scanning of the electron beam has been demonstrated in the fourth generation medical and security Computed Tomography systems and described in Scanning X-ray radiation, U.S. Pat. No. 7,864,924, which is incorporated herein by reference.

We disclose an X-ray backscatter radiography technique for imaging of cargo, vehicles, air containers, small ships, parcels. This method can also improve the performance of very low radiation body scanners systems.

This embodiment is based on the intrapulse modulation of the electron beams energy of the X-ray source, a tiled array of fast detectors, and algorithm of image "peeling" processing. The underline technique is a significant improvement over the currently available backscatter radiography systems. The application of this method will provide better penetration and image resolution, and better ability to discern materials with the different atomic number within closed volume.

Sub-MeV Electron RF Linac with Energy Ramping

The acceleration in RF field is based on the principle that while particles travel, the phase of RF field changes so that the beam always sees the accelerating field. Thus, it is very important to maintain the synchronism between the beam and the RF field. If there is a mismatch between the particle and wave, particles start to oscillate in phase space. If the mismatch is large enough, particles can be lost. Before the electron beam reaches the velocity close to the speed of light (>~4 MeV), where it doesn't have phase oscillation, it is very vulnerable to the RF field parameters.

If the sub-MeV electron linac with energy ramp is required, the design must provide phase acceptance for the beams with the beam velocity profiles that change dramatically from one energy regime to another. Multi-cell accelerating structures that are usually used in industrial linacs for their efficiency will not be able to provide the required acceptance for all energies and their efficiency will drop dramatically if the beam velocity profile becomes different from the wave velocity profile.

One of the solutions that can provide the required velocity acceptance can be a single-gap RF cavity which, if designed properly, can provide the acceptance for the full velocity range. In this case, the cathode can be attached directly to the cavity, so there's DC voltage source. Such an approach is well known, and used in RF electron guns.

The foregoing descriptions of embodiments have been presented for purposes of illustration and exposition. They are not intended to be exhaustive or to limit the embodiments to the precise forms disclosed. Obvious modifications or variations are possible considering the above teachings. The embodiments are chosen and described to provide the best illustrations of principles and practical applications, and to thereby enable one of ordinary skill in the art to utilize the various embodiments as described and with various modifications as are suited to the use contemplated. All such modifications and variations are within the scope of the appended claims when interpreted in accordance with the breadth to which they are fairly, legally, and equitably entitled.

What is claimed is:

1. An inspection system for inspecting an object in motion relative to the inspection system comprising:
   an X-ray source configured to emit a pencil beam onto said object wherein said pencil beam comprising X-rays as a sequence of energy and current modulated X-ray pulses;
   wherein said X-ray pulses are generated by Bremsstrahlung;
   said X-ray source further configured to produce a signal encoding the instantaneous energy and current of said energy and current modulated X-ray pulses;
   a scanning apparatus configured to raster-scan said X-ray pencil beam over said object in the direction perpendicular to the direction of relative motion of said object;
   said scanning apparatus further providing a signal encoding the instantaneous position information of said X-ray pencil beam;
   a detector that creates a detector signal wherein said detector signal is a measure of the instantaneous intensity of backscatter radiation formed in response to the X-rays encountering said object;
   said detector rigidly coupled in position to said X-ray source;
   said detector having a response time shorter than the duration of said X-ray pulse;
   a signal encoding the instantaneous position or said X-ray source relative to said object;
   a data acquisition system acquiring a recorded data wherein said recorded data comprises simultaneously recording said detector signal and said signal encoding the instantaneous X-ray energy and current and said signal encoding the instantaneous position of said X-ray pencil beam and said signal encoding the instantaneous position of said X-ray source relative to said moving object;
   a computer receiving said recorded data;

said computer configured to iteratively compute layer by layer electron density and thickness of materials forming said object.

2. The system of claim 1 wherein said X-ray pulses have a uniformly ramping energy temporal profile.

3. The system of claim 1 wherein said X-ray pulses have a triangular energy temporal profile.

4. The system of claim 3 wherein said X-ray pulses have a half-sine energy temporal profile.

5. The system of claim 1 wherein said X-ray pulses have an increasing energy temporal profile.

6. The system of claim 1 wherein said X-ray pulses have a decreasing energy temporal profile.

7. The system of claim 1 wherein said X-ray source comprises an electrostatic X-ray tube.

8. The system of claim 1 wherein said X-ray source comprises a RF electron accelerator.

9. The system of claim 7 wherein said electrostatic X-ray tube modulates electron energy greater than 50 keV and less than 450 keV.

10. The system of claim 8 wherein said RF electron accelerator modulates electron energy greater than 260 keV and less than 2.0 MeV.

11. The system of claim 1 wherein said detector has a response time less than one fifth of the duration of said X-ray pulses.

12. The system of claim 1 wherein said detector has a response time less than one twentieth of the duration of said X-ray pulse.

13. A method for inspecting an object comprising:
an X-ray source generating X-rays as a pencil beam of energy modulated X-ray pulses incident upon said object;
said object in relative motion to said X-rays beam;
said X-ray source further configured to produce a signal encoding the instantaneous energy and current of said energy and current modulated X-ray pulse;
raster-scanning said X-ray pencil beam over said object in the direction perpendicular to the direction of motion of said object;
creating a detector signal wherein said detector signal is configured to be a measure of the instantaneous intensity of backscatter formed in response to the X-rays encountering said object;
said detector signal having a response time shorter than the duration of said X-ray pulses;
a signal encoding the instantaneous position of said X-ray pencil beam relative to said object;
acquiring a recorded data wherein said recorded data includes simultaneously recording said detector signal and said signal encoding the instantaneous X-ray energy and current, and said signal encoding the instantaneous position of said pencil beam and the instantaneous position of said X-ray pencil beam relative to said moving object;
iteratively computing layer by layer the electron density and thickness of layers of materials forming the object.

14. The method of claim 13 further comprising computing depth dependent images of said object based on said electron density and thickness of layers of materials forming the object.

15. A method for determining material composition of an object comprising:
said object comprising a first material in a first layer and a second material in a second layer;
a beam directed onto said object wherein said beam comprising X-rays as a sequence of pulses of time dependent energy modulated X-rays;
wherein said beam comprises a time dependent Bremsstrahlung X-ray pulse;
producing a signal related to said time dependent instantaneous energy of said beam;
producing a signal that is a measure of the time dependent instantaneous intensity of backscatter formed in response to said beam directed onto said object;
segmenting said backscatter response into at least two energy regions, a first X-ray energy region and a second X-ray energy region;
wherein said first X-ray energy region corresponds to low energy components;
wherein said second X-ray energy region corresponds to high energy components;
estimating the areal electron density of said second layer from the slope of said backscatter response;
estimating from the slope of said backscatter response measured for said first X-ray energy region a using said lookup table estimate a material attenuation coefficient for said first layer; using said estimated material attenuation coefficient for said first layer as input in computing a contribution to backscatter X-rays from said first layer of first material for said second energy region of X-rays;
correcting said backscatter response in said X-ray second energy region for said contribution from said first layer of said first material;
using said corrected second energy region X-ray data set to calculate an electron density of said second layer from said corrected data;
and determining material composition of said first and second layers.

16. The method of claim 15 further comprising raster-scanning said beam over said object in the plane perpendicular to the direction of said beam.

17. The method of claim 15 wherein estimating the material composition of said object comprises evaluating the position of the slope of said detector signal between said low and high energy components.

18. The method of claim 15 wherein said signal related to the instantaneous energy of said beam has a response time less than one fifth of the duration of said pulse of time dependent energy modulated X-rays.

19. The method of claim 15 further comprising:
said object further comprising a third material in a third layer; segmenting said backscatter response into at least three energy regions, said first X-ray energy region and said X-ray second energy region and a third X-ray energy region; wherein said third X-ray energy region corresponds to a higher X-ray energy region of said pulse of time dependent energy modulated X-rays than said second X-ray energy region;
using said backscatter response measured for said first X-ray energy region and said second energy region estimating a material attenuation coefficient for said first layer and for said second layer;
using said estimated material attenuation coefficient for said first and second layers as input in computing a contribution to backscatter X-rays from said first and second layers for said third energy region of X-rays;
correcting said backscatter response in said X-ray third energy region for said contribution from said first and second layers;

using said corrected third energy region X-ray data set to calculate an electron density of said third layer from said corrected data;

and determining material composition of said third layer.

20. The method of claim 15 wherein said object is in relative motion to said beam.

* * * * *